(12) United States Patent
Coyle

(10) Patent No.: US 6,743,208 B1
(45) Date of Patent: Jun. 1, 2004

(54) OCCLUSION BALLOON CATHETER WITH DISTAL VALVE

(75) Inventor: James Coyle, Somerville, MA (US)

(73) Assignee: Medtronic Vascular, INC, Santa Rosa, CA (US)

( * ) Notice: Subject to any disclaimer, the term of this patent is extended or adjusted under 35 U.S.C. 154(b) by 0 days.

(21) Appl. No.: 10/465,085

(22) Filed: Jun. 19, 2003

(51) Int. Cl.⁷ .............................................. A61M 5/178
(52) U.S. Cl. .............................. 604/164.13; 604/99.02; 604/167.03; 604/167.06; 600/585; 600/114; 606/192
(58) Field of Search .............................. 604/523, 99.01, 604/99.02, 164.01, 164.02, 164.13, 167.01, 167.03, 167.06, 171, 164.1, 101.04; 600/114–116, 585; 606/191–200

(56) References Cited

U.S. PATENT DOCUMENTS

| | | | | |
|---|---|---|---|---|
| 4,964,409 A | * | 10/1990 | Tremulis | 600/434 |
| 5,242,394 A | * | 9/1993 | Tremulis | 604/96.01 |
| 5,423,742 A | * | 6/1995 | Theron | 604/28 |
| 5,520,645 A | | 5/1996 | Imran et al. | |
| 6,050,972 A | * | 4/2000 | Zadno-Azizi et al. | 604/97.01 |
| 6,090,083 A | | 7/2000 | Sell et al. | |
| 6,355,014 B1 | | 3/2002 | Zadno-Azizi et al. | |
| 6,475,185 B1 | | 11/2002 | Rauker et al. | |
| 6,500,166 B1 | | 12/2002 | Zadno Azizi et al. | |
| 6,544,276 B1 | | 4/2003 | Azizi | |
| 2002/0133117 A1 | | 9/2002 | Zadno-Azizi et al. | |
| 2003/0055398 A1 | | 3/2003 | Imran | |

* cited by examiner

Primary Examiner—Brian L. Casler
Assistant Examiner—Jeremy Thissell
(74) Attorney, Agent, or Firm—Cardinal Law Group

(57) ABSTRACT

The present invention provides a system for treating a blood vessel. The blood vessel treatment system includes a hollow guidewire having a central lumen, an occlusion balloon attached proximate to a distal end of the hollow guidewire, and an inflation catheter slidable over the hollow guidewire. An annular inflation lumen formed between the inflation catheter and the hollow guidewire fluidly communicates with the central lumen of the hollow guidewire, allowing inflation fluid to flow through the annular inflation lumen and into a distal portion of the central lumen to inflate the occlusion balloon.

20 Claims, 10 Drawing Sheets

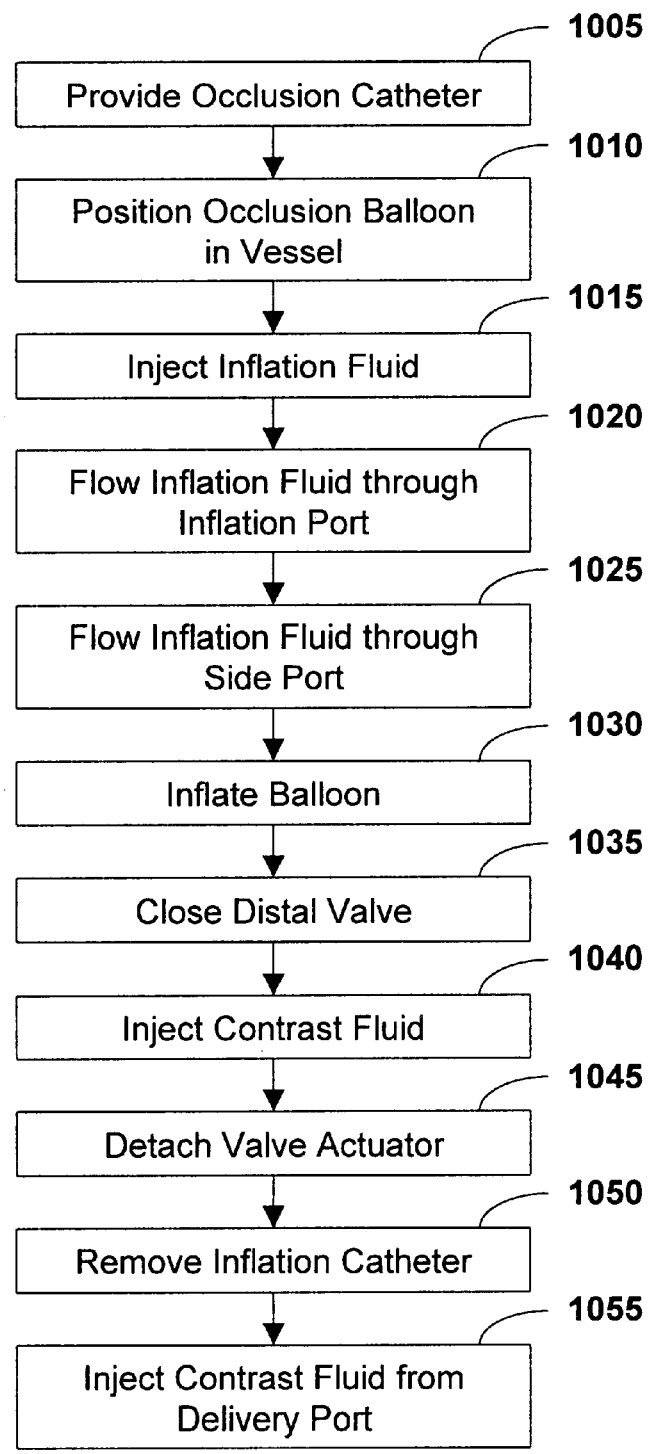

OCCLUSION BALLOON CATHETER WITH DISTAL VALVE

FIELD OF THE INVENTION

This invention relates generally to catheters and guidewire deployment of catheter-based treatment tools. More specifically, the invention relates to an occlusion catheter with a distal valve.

BACKGROUND OF THE INVENTION

Minimally invasive intravascular procedures are revolutionizing many surgical specialties including cardiac surgery, and are becoming common in the treatment of vascular disease. Today, balloon angioplasty is commonly used to alleviate stenotic lesions in blood vessels, thereby reducing the need for heart bypass operations. Medical balloon catheters also have been proven efficacious in treating a wide variety of blood vessel disorders such as intravascular restrictions due to atherosclerosis or restenosis.

Vascular stenoses, which may be partially or totally occluded, are often characterized by having a mineral component. A variety of different protocols have been developed for treating vascular diseases with these calcified areas. The treatment methodologies generally involve mechanically removing or reducing the size of the stenosis, mechanical debridement, atherectomy, balloon angioplasty, stenting, and bypass surgery procedures.

In exemplary intravascular procedures, a balloon catheter dilates an intravascular restriction, or an atherectomy catheter removes the restriction. Unfortunately, the intravascular procedures associated with these devices may result in embolic particles being dislodged while the restriction is dilated or cut. In addition, the dislodged embolic particles may move downstream from the area of restriction and cause another embolism to form, which, in turn, could compromise the flow of blood to the surrounding tissue.

In response to this problem of dislodged particles, occlusion balloon catheters and aspiration catheters have been developed to help prevent dislodged embolic particles from entering the blood stream. The occlusion balloon catheter blocks or impedes blood flow while the aspiration catheter aspirates and removes embolic particles from the area of the stenosis.

Proposed aspiration methods that use an aspiration catheter are described in "Methods for Reducing Distal Embolization", Imran, U.S. Patent Publication 20030055398 published Mar. 20, 2003. One method crosses the stenosis with a guidewire while aspirating blood, so that blood flows past the stenosis and emboli debris are removed, after which the primary treatment of the stenosis can begin. Another method, which treats a vessel stenosis, involves advancing a guidewire and a first catheter to a location near the stenosis, aspirating particles through the lumen of the first catheter; delivering a therapy catheter to a location near the stenosis; and performing treatment on the stenosis using the therapy catheter.

Occlusion balloon catheters are usually used in conjunction with other catheters, particularly an aspiration catheter. An occlusion catheter, which often includes an elongated shaft and a distally mounted occlusion or attenuation balloon, typically extends through a lumen of a primary dilation or atherectomy catheter. The balloon is advanced through a vessel, positioned distal to the site of the stenosis, and temporarily inflated to prevent embolic particles from flowing downstream as the occlusive restriction is being dilated or cut. After the restriction has been treated, the primary catheter can be removed from over the guidewire of the occlusion balloon catheter. An aspiration catheter can then be advanced proximal to the stenosis to reduce or eliminate the blockage by aspirating the treatment site. Once the embolic particles have been aspirated, the occlusion balloon is deflated and removed from a patient.

An exemplary occlusion catheter and associated occlusion and aspiration method uses a catheter and a guidewire having a hollow shaft and a flexible, shapeable guidewire distal tip. A deflated elastomeric occlusion balloon is located at the proximal end of the distal tip of the guidewire. The distal tip of the guidewire and the balloon crosses the lesion, an inflation device is attached to the proximal end of the catheter, and the occlusion balloon is inflated with dilute contrast agent. Following the inflation of the balloon, an angiogram using fluoroscopy may be taken to ensure complete occlusion by the balloon. The hollow guidewire can be used to infuse or deliver fluoroscopic material or therapeautic agents to the treatment site. The inflation device can be removed from the proximal end of the wire while the occlusion balloon remains inflated, and then a stent-delivery catheter maybe exchanged to provide percutaneous transluminal angioplasty. With the occlusion balloon inflated, balloon angioplasty or stenting may be performed. The embolic particles that are released during a coronary angioplasty or stenting procedure remain trapped in the artery upstream of the occlusion balloon. Following the removal of the angioplasty balloon catheter, an aspiration catheter may be introduced over the guidewire to aspirate the particles.

A specific example of an occlusion catheter is described by Rauker and others in "Occlusion Device", U.S. Pat. No. 6,475,185 issued Nov. 5, 2002. The occlusion device includes an elongated tubular shaft having an inflatable balloon disposed near the elongate shaft distal end with a proximal seal of a sufficiently small profile to allow a second catheter to pass over the distal occlusion device while the inflatable balloon remains uninflated. One occlusion device includes an elongated fluid displacement rod within the elongated shaft of the occlusion device, providing both a fluid pressure source and a seal.

Controlling the flow and sealing the inflation fluid into the balloon of the occlusion catheter can be challenging. Sell and others have used a valve of an inner tube that is closely fit into an outer tube, as disclosed in "Low Profile Valve and Balloon Catheter", U.S. Pat. No. 6,090,083 issued Jul. 18, 2000. The low-profile inflation valve includes a first thermoplastic tube with at least one region of decreased inner diameter, and a structure, which may be a tube, movably located inside the lumen. The region of decreased inner diameter of the first tube forms a seal with a portion of the structure.

Many medical procedures require that more than one catheter be advanced in and out of a body vessel. Various solutions have been suggested to allow a more rapid, safe, and unobstructed exchange of catheters. Improvements to catheter designs, fittings, valves, other parts of catheters, guidewires, and balloons have been suggested. One proposed improvement in the exchanging of catheters is to have a removable inflation fitting on the inflation tube that supplies fluid to a catheter balloon, as described in "Low Profile Angioplasty Catheter and/or Guide Wire and Method", Imran et al., U.S. Pat. No. 5,520,645 issued May 28, 1996. The inflation fitting is removable so that the proximal extremity of the catheter is free of obstruction and another balloon catheter can be advanced over the proximal extremity.

Improvements to a balloon occlusion catheter and an associated method are proposed in "Low Profile Catheter Valve and Inflation Adaptor", Zadno-Azizi et al., U.S. Patent Application 20020133117 published Sep. 19, 2002; "Exchange Method for Emboli Containment", Zadno-Azizi et al., U.S. Pat. No. 6,544,276 issued Apr. 8, 2003; "Method of Emboli Protection using a Low Profile Catheter", Zadno-Azizi et al., U.S. Pat. No. 6,500,166 granted Dec. 31, 2002; and "Low Profile Catheter Valve", U.S. Pat. No. 6,355,014, Zadno-Azizi et al., granted Mar. 12, 2002. The catheter includes a low-profile catheter valve with a movable sealer portion positioned within the inflation lumen of a catheter. The sealer portion forms a fluid tight seal with the inflation lumen by firmly contacting the entire circumference of a section of the inflation lumen. The sealer portion is positioned proximate to a side-access inflation port on the catheter, establishing an unrestricted fluid pathway between the inflation port and an inflatable balloon on the distal end of the catheter. The sealer portion can be moved to a position distal of the inflation port, thereby preventing fluid from being introduced into or withdrawn from the balloon via the inflation port. An inflation adaptor can be used for moving the sealer portion within the catheter to establish or close the fluid pathway between the inflation port and the inflatable balloon.

There is continued interest in improving minimally invasive treatments for vascular stenoses that use various intravascular catheters and associated devices. Of particular interest is the development of an improved occlusion catheter and associated devices and methods that provide faster inflation and deflation time for the occlusion balloon; improved robustness of the guidewire; more controlled advancement of the guidewire and occlusion balloon when crossing lesions in the vessel; greater control of fluoroscopic dye or other imaging fluid; and better visualization of the vessel after temporary occlusion with the occlusion balloon.

Therefore, it is desirable to have an improved blood vessel treatment system and method for treating vessels in the body, providing the abovementioned desirable improvements that increase the utility and performance of the medical devices used during the treatment of a vascular condition.

SUMMARY OF THE INVENTION

One aspect of the invention provides a system for treating a blood vessel. The blood vessel treatment system includes a hollow guidewire having a central lumen, an occlusion balloon attached proximate to a distal end of the hollow guidewire, and an inflation catheter slidable over the hollow guidewire. An annular inflation lumen formed between the inflation catheter and the hollow guidewire fluidly communicates with the central lumen of the hollow guidewire. Inflation fluid is allowed to flow through the annular inflation lumen and into a distal portion of the central lumen to inflate the occlusion balloon. The system may include a distal valve coupled to the hollow guidewire to control the flow of inflation fluid between the hollow guidewire and the occlusion balloon.

Another aspect of the invention is an occlusion catheter for blocking flow through a vessel of a body. The occlusion catheter includes a hollow guidewire having a central lumen, an occlusion balloon attached proximate to a distal end of the hollow guidewire, and an inflation catheter slidable over the hollow guidewire. An annular inflation lumen formed between the inflation catheter and the hollow guidewire fluidly communicates with the central lumen of the hollow guidewire, allowing inflation fluid to flow through the annular inflation lumen and into a distal portion of the central lumen to inflate the balloon.

Another aspect of the invention is a method for treating a vascular condition. The method provides an occlusion catheter, which includes a hollow guidewire having a central lumen, an occlusion balloon attached proximate to a distal end of the hollow guidewire, and an inflation catheter slidable over the hollow guidewire. An inflation fluid is injected through an annular inflation lumen formed between the inflation catheter and the hollow guidewire. The inflation fluid flows through an inflation port into a distal portion of the central lumen and through a side port positioned between the central lumen of the hollow guidewire and the occlusion balloon, thereby inflating the occlusion balloon.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE DRAWINGS

Various embodiments of the present invention are illustrated by the accompanying figures, wherein:

FIG. 10 is a flow diagram of a method for treating a vascular condition, in accordance with one embodiment of the current invention.

DETAILED DESCRIPTION OF THE PRESENTLY PREFERRED EMBODIMENTS

Figure 1:
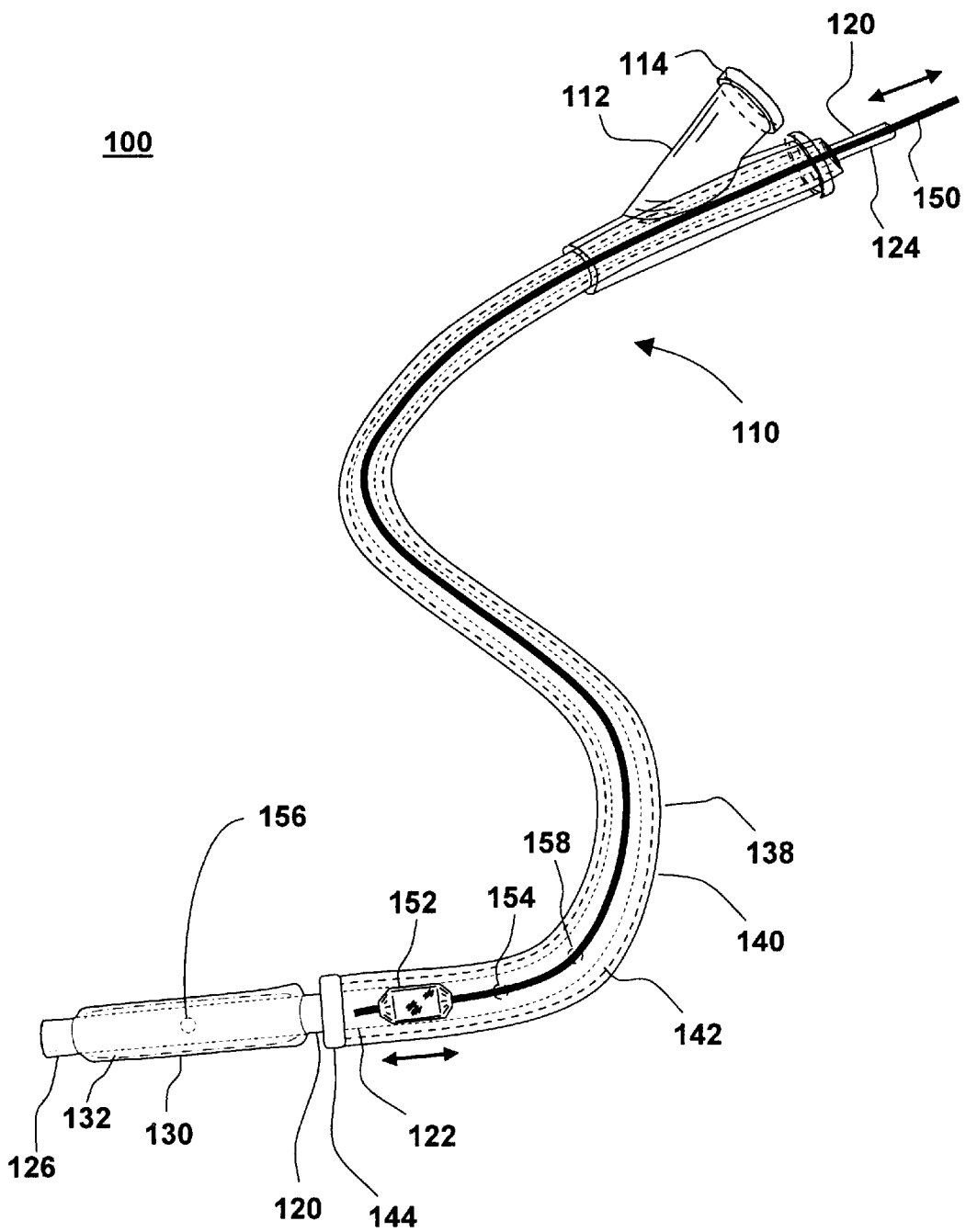
FIG. 1 is an illustration of a system for treating a vessel in a body, in accordance with one embodiment of the current invention.

FIG. 1 illustrates a system for treating a vessel in a body, in accordance with one embodiment of the present invention at 100. Vessel treatment system 100 includes an occlusion catheter 110. Occlusion catheter 110 comprises hollow guidewire 120, distal occlusion balloon 130 attached to hollow guidewire 120, and an inflation catheter 140 slidable over hollow guidewire 120.

Occlusion catheter 110 is generally used to temporarily block or occlude a vessel in the body to stop the local flow of blood and fluids while medical procedures or treatments are completed within the vessel. While occlusion catheter 110 anchors hollow guidewire 120 to a vascular wall, hollow guidewire 120 may be used to guide to the treatment area other medical devices such as an angioplasty or dilation catheter, an atherectomy catheter, a stent-delivery catheter, a drug-delivery catheter, an ultrasound device, a measurement device, a laser catheter, an imaging catheter, a treatment catheter or a therapy catheter.

Occlusion catheter 110 can be used, for example, to rapidly inflate occlusion balloon 130 and temporarily occlude a blood vessel; to aspirate emboli and other debris in the blood vessel proximal to the temporary occlusion; to inject dye or contrast fluid into the stagnant fluid for stenosis visualization after vessel occlusion; and to provide an anchored guidewire for the subsequent deployment of a treatment catheter such as a stent-delivery catheter. An inflation connector 112 coupled to occlusion catheter 110 may have one or more ports 114 through which fluid is injected or aspirated for procedures such as the injection of inflation fluid into occlusion balloon 130, the injection of dye into a vessel for visualization, or the aspiration of fluids and debris from within a vessel.

Hollow guidewire 120, is a generally long, flexible, elongate tubular member with central lumen 122. An exemplary hollow guidewire 120 may be made from a tube of stainless steel, nitinol, or other suitable tubing material sometimes referred to as a hypotube. Suitable hypotubing may have a small outer diameter on the order of, for example, 0.014 inches, and a small inner diameter on the order of 0.008 inches. The length of hollow guidewire 120 may be on the order of 300 cm, allowing over-the-wire (OTW) catheters to be inserted into the body once hollow guidewire 120 is in place. In another example, hollow guidewire 120 may be on the order of 180 cm in length, suitable for guiding rapid-exchange type treatment catheters and zipper-type catheters. At proximal end 124 of hollow guidewire 120, central lumen 122 is physically accessible for injecting fluid and inserting small wires such as core wires. At distal end 126 of hollow guidewire 120, central lumen 122 is typically sealed and generally not physically accessible. Occlusion balloon 130 is attached proximate to distal end 126 of hollow guidewire 120.

Occlusion balloon 130 is generally spherical or cylindrical elastic membrane having proximal and distal ends attached to an outside surface of hollow guidewire 120, such that occlusion balloon 130 may be inflated and enlarged by filling an interior region 132 of occlusion balloon 130 with an inflation fluid without leakage either through the elastic membrane material or through the attached proximal and distal ends of occlusion balloon 130. Occlusion balloon 130 may comprise, for example, one or more layers of expandable material such as polyurethane, radiopaque polyurethane material, thermoplastic polyurethane elastomers, aliphatic polyurethanes, aromatic polyurethanes, styrene-ethylene-butylene-styrene (SEBS) block copolymer, thermoplastic elastomers, low-density polyethylene, polyethylene terephthalate, polyethylene terephthalate glycol, silicone, copolymer of polyurethane and silicone, natural rubber, synthetic rubber, thermoplastic polyamide, nylon, latex, polyethylene, polyisoprene, polyisobutylene, thermoplastic elastomers, an elastomeric material, or combinations thereof. Attachment of occlusion balloon 130 to hollow guidewire 120 may be achieved with suitable adhesive, heat bonds, mechanical couplers, wire wraps, bands, or other types of balloon attachment techniques. When the inflation fluid is pushed into occlusion balloon 130, the balloon enlarges in proportion to the amount of the fluid inside. When deployed in the body, occlusion balloon 130 is generally enlarged to fill region of the vessel and temporarily block flow through the vessel.

A removable inflation catheter 140 provides pathway for inflation fluid to fill occlusion balloon 130. Inflation catheter 140 generally slides over hollow guidewire 120. When placed over hollow guidewire 120, occlusion catheter 110 becomes more rigid, enhancing its tactile feel and control with an increased robustness against kinking of hollow guidewire 120.

In one embodiment, inflation catheter 140 is slid and abutted against mechanical stop 144 that is coupled to an exterior surface of hollow guidewire 120 proximal to occlusion balloon 130. Mechanical stop 144 limits axial displacement of inflation catheter 140 over hollow guidewire 120. In other embodiments, mechanical stop 144 cooperates with a distal end of inflation catheter 140 to form a distal seal.

Mechanical stop 144 may comprise a relatively inelastic material such as stainless steel, nitinol, tantalum, MP35N cobalt alloy, platinum, titanium, a thermoset plastic, a suitable biocompatible alloy, a suitable biocompatible material, or a combination thereof. Mechanical stop 144 may be made from or include a radiopaque marker comprising material such as platinum, barium, tantalum, iridium, gold or a combination thereof. Mechanical stop 144 is typically a collar or a shaped tube wrapping around a portion of hollow guidewire 120 and typically less than a few millimeters in length with an outer diameter that prevents excessive axial movement of inflation catheter 140 over hollow guidewire 120, while retaining a sufficiently low profile, preferably less than the diameter of the collapsed balloon. In one embodiment, mechanical stop 144 is positioned adjacent to a proximal end of occlusion balloon 130. In another embodiment, mechanical stop 144 is positioned a prescribed distance from the proximal end of occlusion balloon 130 for increased flexibility of hollow guidewire 120 near distal end 126 for easier navigation through tortuous vasculature.

During medical procedures with occlusion catheter 110, inflation catheter 140 may be initially positioned over hollow guidewire 120 to form an annular inflation lumen 142 between an outer surface of hollow guidewire 120 and an inner surface of inflation catheter 140. Annular inflation lumen 142 fluidly communicates with central lumen 122 of hollow guidewire 120, allowing inflation fluid to flow through annular inflation lumen 142 and into a distal portion of central lumen 122 to inflate occlusion balloon 130. In one example, annular inflation lumen 142 fluidly communicates with central lumen 122 of hollow guidewire 120 through an inflation port 154 positioned between annular inflation lumen 142 and central lumen 122 of hollow guidewire 120, generally at a point near the distal end of occlusion catheter 110, proximal to balloon 130. Annular inflation lumen 142 provides a larger cross-sectional area than central lumen 122 of hollow guidewire 120, allowing for faster inflation and deflation of occlusion balloon 130 when compared to the time required to deliver fluid through central lumen 122 along the entire length of hollow guidewire 120. With a distal valve, only a shorter distal portion of central lumen 122 fluidly communicates with occlusion balloon 130. Inflation port 154 may comprise, for example, a hole, an aperture, or a series of holes and apertures through a sidewall of hollow guidewire 120.

To inflate occlusion balloon 130, central lumen 122 fluidly communicates with interior region 132 of occlusion balloon 130 through side port 156 in hollow guidewire 120, side port 156 being positioned between central lumen 122 and occlusion balloon 130. Side port 156 may comprise, for example, a hole or series of holes in a sidewall of hollow guidewire 120 between the proximal and distal ends of occlusion balloon 130. Side port 156 allows inflation fluid from central lumen 122 to flow into interior region 132 of occlusion balloon 130.

The distal end of inflation catheter 140 may be located close to the proximal end of occlusion balloon 130, though in some cases the distal end of inflation catheter 140 is located a distance further from the proximal end of occlusion balloon 130, thereby increasing the flexibility of hollow guidewire 120 and narrowing the effective cross-sectional area of the distal end of occlusion catheter 110 during the routing and positioning of occlusion balloon 130.

When occlusion balloon 130 is inflated, inflation catheter 140 may be slidably removed from hollow guidewire 120, allowing other treatment catheters to be placed over hollow guidewire 120 while blood flow in the vessel is blocked. To avoid inflation fluid from leaking out of inflation port 154 when inflation catheter 140 is removed, a distal valve coupled to hollow guidewire 120 controls the flow of inflation fluid between hollow guidewire 120 and occlusion balloon 130.

In one example of a distal valve, sealing plug 152 is attached near a distal end of core wire 150. Core wire 150 may comprise, for example, a thin wire or rod of stainless steel, nitinol, or other suitably flexible and strong material. Operating like a plunger, core wire 150 is slidably disposed within hollow guidewire 120. Sealing plug 152 may comprise, for example, a silicone, an epoxy, or other wear-resistant, semi-compliant material. An axial displacement of a proximal end of core wire 150 displaces sealing plug 152 at a distal end of core wire 150 to open and close the distal valve. To close the distal valve, core wire 150 is pushed further into central lumen 122 of hollow guidewire 120 so that sealing plug 152 covers inflation port 154 or is positioned somewhere between inflation port 154 and side port 156. To open the distal valve, core wire 150 is retracted slightly to axially displace sealing plug 152, uncovering inflation port 154 so that inflation fluid may flow through inflation port 154 and to or from occlusion balloon 130 through a distal portion of central lumen 122 between inflation port 154 and side port 156. Axial displacement of the proximal end of core wire 150 may be controlled, for example, with a detachable valve actuator coupled to proximal end 124 of hollow guidewire 120 to actuate the distal valve.

Occlusion catheter 110 may also be used to inject contrast fluid into the blood vessel during the positioning or after the inflating of occlusion balloon 130 in order to visualize and verify the location of a stenosis, blockage, or other therapeutic condition within the blood vessel. The contrast fluid may also serve as inflation fluid to inflate occlusion balloon 130.

In one embodiment, an additional contrast fluid lumen 138 may be attached to or integrally formed within inflation catheter 140 to inject contrast fluid into the blood vessel. In another embodiment, inflation port 154 may be used to inject contrast fluid into the blood vessel when the distal valve is closed and inflation catheter 140 is removed, by pushing contrast fluid through central lumen 122 from proximal end 124 of hollow guidewire 120 to inflation port 154. Alternatively, additional contrast fluid injection ports 158 may be used to inject contrast fluid from one or more contrast fluid injection ports 158 located proximally to occlusion balloon 130 after occlusion balloon 130 has been inflated and inflation catheter 140 has been removed. In another embodiment, contrast fluid may be injected into the blood vessel proximate the inflated occlusion balloon 130 by a slight retraction of inflation catheter 140 to physically expose a distal end of annular inflation lumen 142, so that contrast fluid can be injected in large amounts into the blood vessel.

Figure 2:
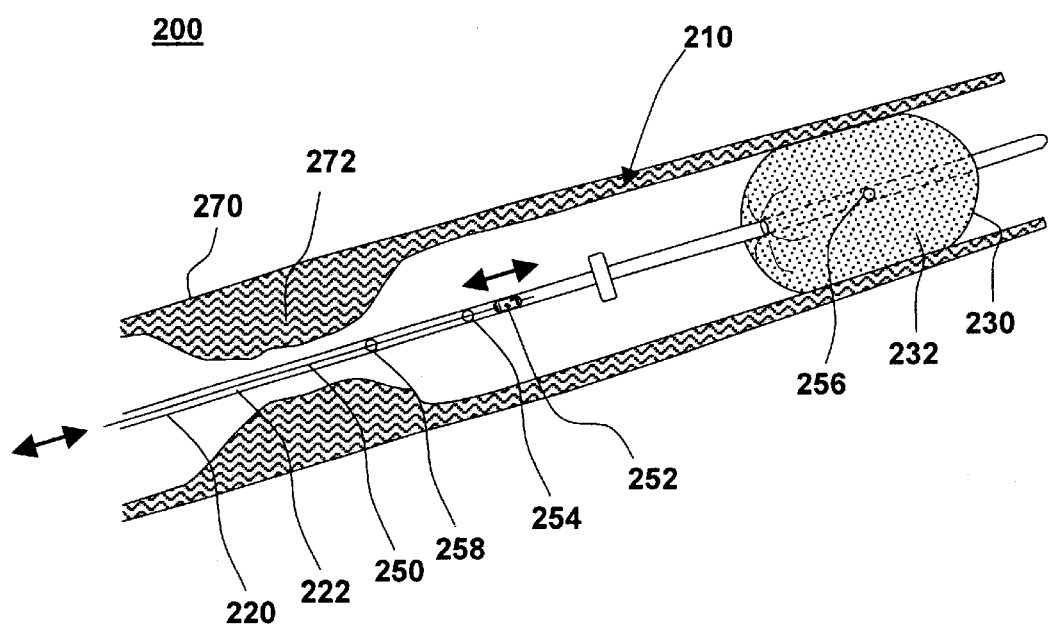
FIG. 2 shows a longitudinal cross-sectional view of a distal end of an occlusion catheter in a stenosed vessel, in accordance with one embodiment of the current invention.

FIG. 2 shows a longitudinal cross-sectional view of a distal end of occlusion catheter 210 in a stenosed vessel, in accordance with one embodiment of the present invention at 200. Occlusion catheter 210 includes an inflatable occlusion balloon 230 attached proximate to a distal end of hollow guidewire 220. A distal valve comprising core wire 250 and sealing plug 252 is coupled to hollow guidewire 220 to control the flow of inflation fluid between central lumen 222 of hollow guidewire 220 and occlusion balloon 230. Core wire 250 is slidably disposed within hollow guidewire 220. An axial displacement of a proximal end of core wire 250 displaces sealing plug 252 at a distal end of core wire 250 to open and close the distal valve. In the embodiment illustrated, inflation fluid has been injected from central lumen 222 through side port 256 into an interior region 232 of occlusion balloon 230, expanding occlusion balloon 230 to a diameter sufficiently large to temporarily occlude vessel 270 in the body. Sealing plug 252 is positioned distal to an inflation port 254 to maintain inflation fluid within occlusion balloon 230. Blood flow within vessel 270 is temporarily blocked so that treatments can be applied to, for example, stenosis 272.

In FIG. 2, an inflation catheter for inflating occlusion balloon 230 has been removed, allowing other treatment catheters such as a stent-delivery catheter to be slid over hollow guidewire 220 and rapidly positioned as desired within vessel 270. With the inflation catheter removed, inflation port 254 and any additional contrast-fluid injection ports 258 can be used to inject radioscopic or fluoroscopic contrast fluid into vessel 270, which helps a medical specialist to fluoroscopically locate, identify and visualize targeted stenosis 272 and/or other treatable sites within vessel 270. Contrast fluid may flow to a distal end of hollow guidewire 220 through central lumen 222 while core wire 250 is disposed within hollow guidewire 220 and sealing plug 252 maintains inflation fluid within occlusion balloon 230.

Figure 3:
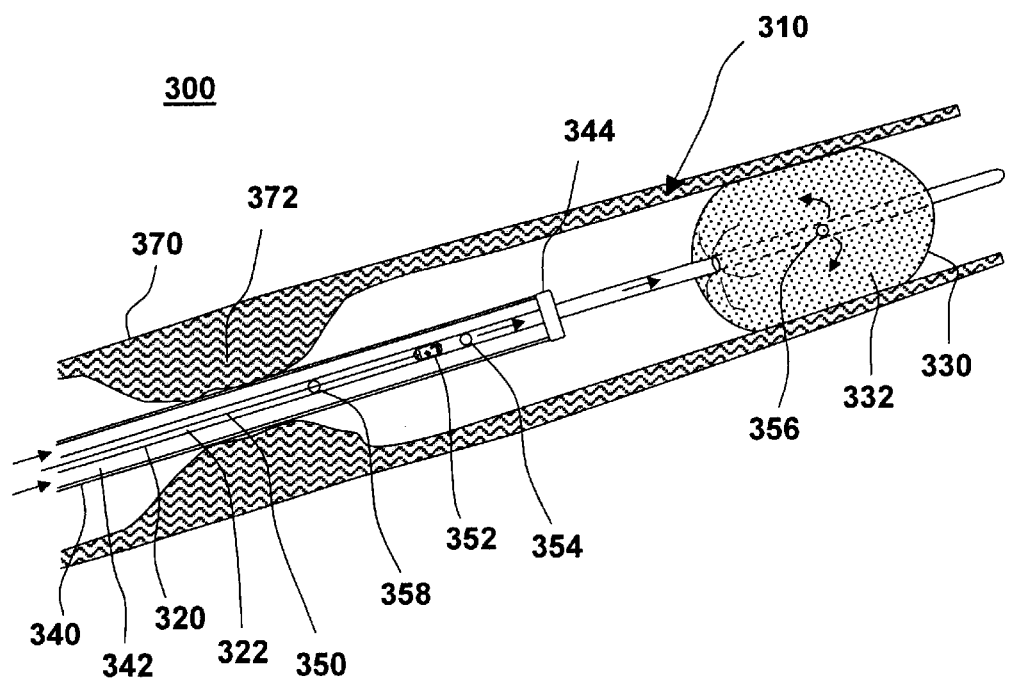
FIG. 3 shows a longitudinal cross-sectional view of a distal end of an occlusion catheter in a stenosed vessel, in accordance with another embodiment of the current invention.

FIG. 3 shows a longitudinal cross-sectional view of a distal end of occlusion catheter 310 in a stenosed vessel, in accordance with one embodiment of the present invention at 300. Occlusion catheter 310 includes hollow guidewire 320 with an inflatable occlusion balloon 330 located near a distal end of hollow guidewire 320, and an inflation catheter 340 slid over hollow guidewire 320.

In this figure, inflation catheter 340 forms an annular inflation lumen 342 between an inner surface of inflation catheter 340 and an outer surface of hollow guidewire 320. Occlusion balloon 330 inflates with inflation fluid that enters at a proximal end of inflation catheter 340 and traverses through annular inflation lumen 342 to inflation port 354. The inflation fluid flows through inflation port 354 into a distal portion of central lumen 322, and then continues to flow through side port 356 positioned between central lumen 322 and occlusion balloon 330, thereby filling and expanding occlusion balloon 330. Mechanical stop 344 located proximal to occlusion balloon 330 provides a seal for annular inflation lumen 342 at the distal end of inflation catheter 340 and limits the travel of inflation catheter 340 over hollow guidewire 320. A distal valve comprising core wire 350 with sealing plug 352 attached near a distal end of core wire 350 is openly positioned so that inflation fluid can ingress through inflation port 354 into central lumen 322 to inflate occlusion balloon 330, thereby temporarily blocking flow of body fluid through vessel 370.

When occlusion balloon 330 is properly inflated, sealing plug 352 is axially displaced into a closed position distal to inflation port 354, so that inflation fluid is retained within interior region 332 of occlusion balloon 330, allowing inflation catheter 340 to be slidably removed from hollow guidewire 320. Treatment catheters can then be slid over hollow guidewire 320 for treating stenosis 372 and other conditions within vessel 370. Additional contrast-fluid injection ports 358 can be used to inject radioscopic or fluoroscopic contrast fluid into vessel 370.

Figure 4:
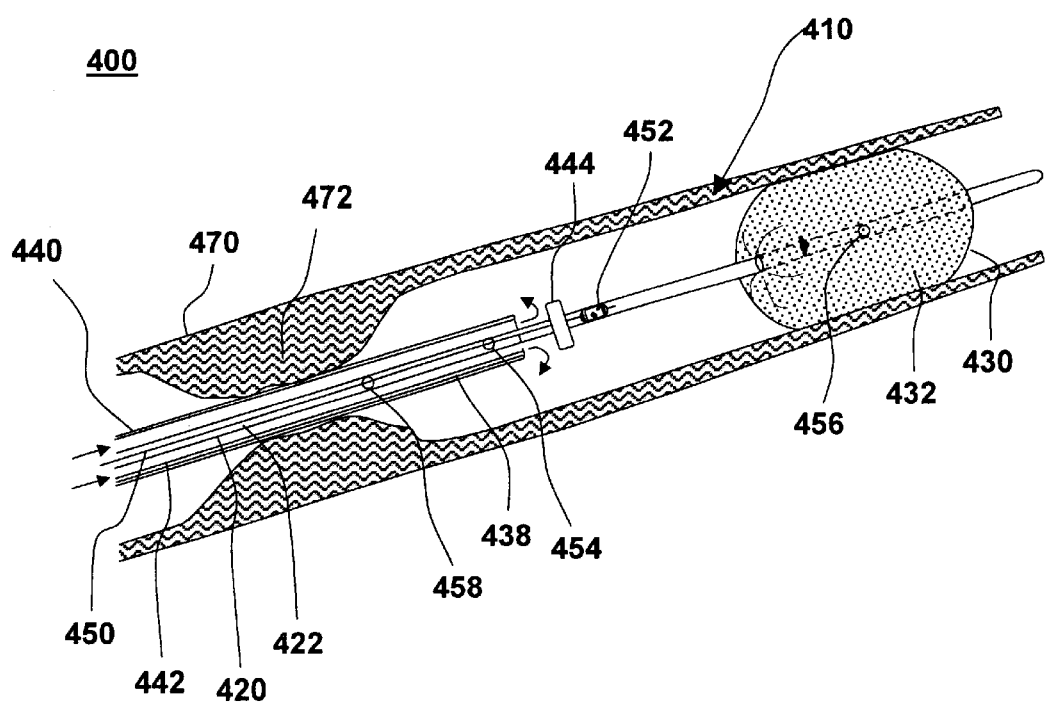
FIG. 4 shows a longitudinal cross-sectional view of a distal end of an occlusion catheter with a slightly retracted inflation catheter, in accordance with one embodiment of the current invention.

FIG. 4 shows a longitudinal cross-sectional view of a distal end of occlusion catheter 410 with a slightly retracted inflation catheter, in accordance with one embodiment of the present invention at 400. Occlusion catheter 410 includes an inflatable occlusion balloon 430 attached near a distal end of hollow guidewire 420. In this figure, inflation fluid has been injected into an interior region 432 of occlusion balloon 430, enlarging occlusion balloon 430, thereby blocking flow through vessel 470 so that stenosis 472 or other condition within vessel 470 can be treated. Inflation fluid is retained within occlusion balloon 430 by the closure of a distal valve, which comprises sealing plug 452 attached at a distal end of core wire 450, with core wire 450 slidably disposed within central lumen 422 of hollow guidewire 420. Sealing plug 452 is positioned to block the flow of inflation fluid from side port 456 to inflation port 454 of hollow guidewire 420.

To accurately image stenosis 472 once the flow of bodily fluid through vessel 470 has been blocked, radiopaque contrast media, also serving as inflation fluid, may be injected into the stagnant fluid within vessel 470 from the distal end of annular inflation lumen 442 by retracting inflation catheter 440 a sufficient distance to break the seal between the end of inflation catheter 440 and mechanical stop 444. Radiopaque contrast media may be injected into the proximal end of inflation catheter 440 and emitted from the distal end of inflation catheter 440. Alternatively, the contrast media may be injected through additional contrast fluid lumen 438 extending the length of inflation catheter 440.

In yet another x-ray visualization technique, radiopaque contrast media may be injected through central lumen 422 of hollow guidewire 420 to inflation port 454 and/or any additional contrast fluid injection ports 458 for injecting into vessel 470 while core wire 450 is disposed within hollow guidewire 420 and sealing plug 452 maintains inflation fluid within occlusion balloon 430. This method may be used when inflation catheter 440 has been slightly retracted, or even if it has been completely removed from hollow guidewire 420.

Figure 5:
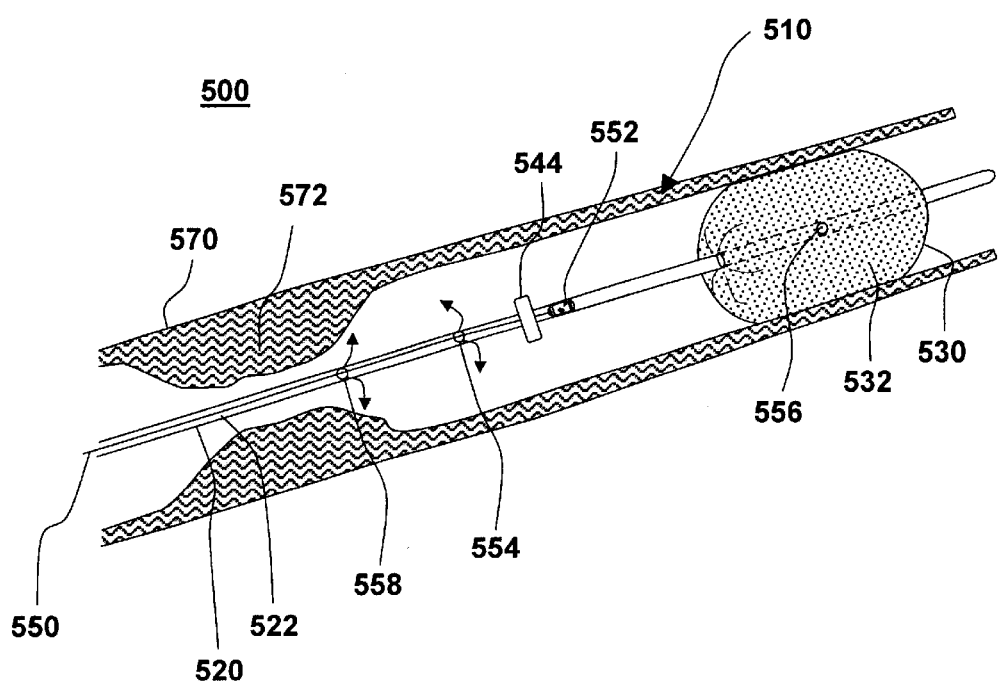
FIG. 5 shows a longitudinal cross-sectional view of a distal end of an occlusion catheter, in accordance with another embodiment of the current invention.

FIG. 5 shows a longitudinal cross-sectional view of a distal end of occlusion catheter 510, in accordance with another embodiment of the present invention at 500. Occlusion catheter 510 includes hollow guidewire 520 having central lumen 522, an inflatable occlusion balloon 530 attached proximate to a distal end of hollow guidewire 520, and mechanical stop 544 coupled near a proximal end of occlusion balloon 530. In this figure, an inflation catheter has been slidably removed from over hollow guidewire 520 to reveal at least one inflation port 554 and at least one contrast fluid injection port 558. Contrast fluid injection port 558 is positioned proximal to inflation port 554, near a distal end of hollow guidewire 520. When the inflation catheter has been removed from hollow guidewire 520, contrast fluid from central lumen 522 can be injected through contrast fluid injection port 558 and/or inflation port 554 into vessel 570. Sealing plug 552, attached near a distal end of core wire 550, retains inflation fluid within interior region 532 of occlusion balloon 530 by blocking a distal portion of central lumen 522 between inflation port 554 and side port 556. The contrast fluid is forced into central lumen 522 at a proximal end and traverses through a proximal portion of central lumen 522 until it is injected from inflation ports 554 and/or contrast injection ports 558. The injected contrast fluid may be used to image stenosis 572 or other conditions within vessel 570.

Figure 6:
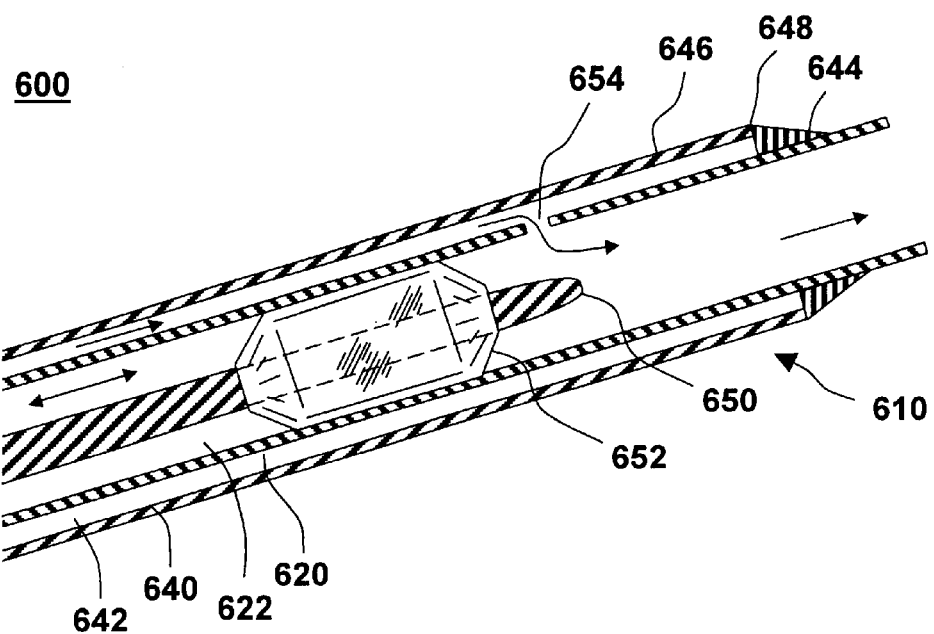
FIG. 6 shows a longitudinal cross-sectional view of a distal end of an occlusion catheter, in accordance with another embodiment of the current invention.

FIG. 6 shows a longitudinal cross-sectional view of a distal end of occlusion catheter 610, in accordance with another embodiment of the present invention at 600. Occlusion catheter 610 shows details of distal seal 648 between a distal end of an inflation catheter 640 and mechanical stop 644. Distal seal 648 blocks inflation fluid traversing through annular inflation lumen 642 between an inner surface of inflation catheter 640 and an outer surface of hollow guidewire 620, preventing inadvertent leakage of inflation fluid into a body vessel surrounding occlusion catheter 610. The inflation fluid flows from annular inflation lumen 642 into a distal portion of central lumen 622 within hollow guidewire 620. Sealing plug 652 attached near a distal end of core wire 650 is retracted from inflation port 654 to allow flow of inflation fluid into an inflatable occlusion balloon (not shown).

In this embodiment, mechanical stop 644 is attached to an outer surface of hollow guidewire 620. Generally in the form of a band or a collar, mechanical stop 644 limits axial travel of inflation catheter 640 at a distal end of hollow guidewire 620, and provides a mating surface against which the distal end 646 of inflation catheter 640 may be pressed and abutted to prevent the flow of fluid through distal seal 648. Distal seal 648 may be held closed, for example, using a removable adapter or a retention mechanism coupled between inflation catheter 640 and hollow guidewire 620 near the proximal end of occlusion catheter 610. The mating surface may be augmented with a compliant or elastic sealing material such as polyurethane, a silicone, or other suitable polymer to aid in the formation of a suitable seal. Alternatively, a radial seal may be formed at distal end 646 of inflation catheter 640 by the inclusion of an elastomeric end cap or a distally mounted internal seal member capable of slidingly sealing along the outer surface of hollow guidewire 620 to provide distal seal 648.

Figure 7:
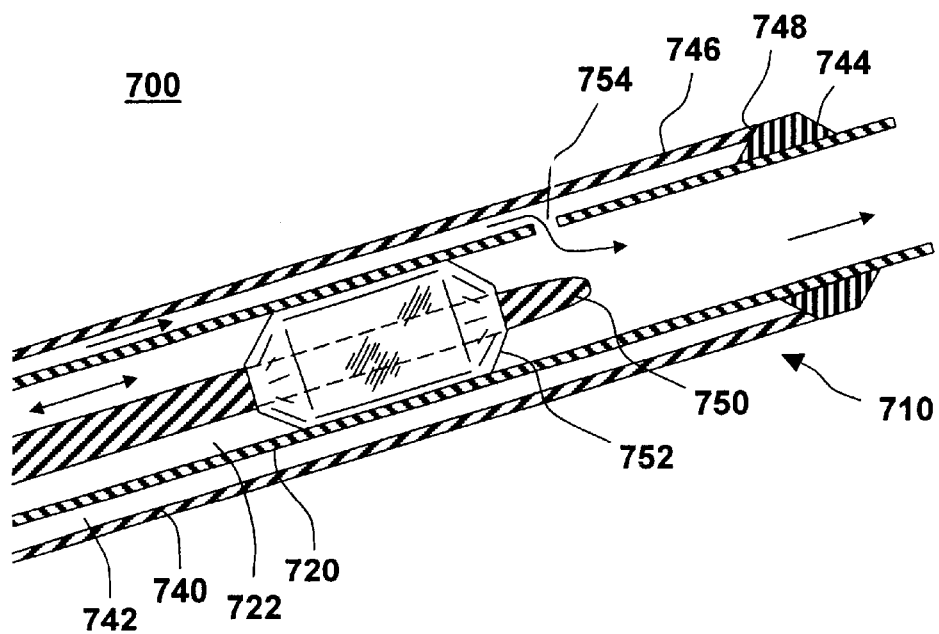
FIG. 7 shows a longitudinal cross-sectional view of a distal end of an occlusion catheter, in accordance with another embodiment of the current invention.

FIG. 7 shows a longitudinal cross-sectional view of a distal end of occlusion catheter 710, in accordance with another embodiment of the present invention at 700. Occlusion catheter 710 includes hollow guidewire 720 with a centrally disposed core wire 750 including sealing plug 752 attached near a distal end of core wire 750 to form a distal valve. The distal valve controls the flow of inflation fluid between inflation port 754 and an inflatable occlusion balloon (not shown). When sealing plug 752 is axially withdrawn, inflation fluid may traverse annular inflation lumen 742 formed between inflation catheter 740 and hollow guidewire 720, flow through inflation port 754 into a distal portion of central lumen 722 of hollow guidewire 720, and inflate an occlusion balloon attached proximate to a distal end of hollow guidewire 720. When sealing plug 752 is axially withdrawn, the balloon may also be deflated by reversing the flow of inflation fluid along the same flow path described above.

Distal seal 748 is formed when distal end 746 of inflation catheter 740 is pressed against mechanical stop 744. In this embodiment, a wedge or tapered surface aids in the formation of distal seal 748 by self-centering the distal end of inflation catheter 740 around a mating surface of mechanical stop 744. The mating surfaces on either the distal end of inflation catheter 740 or mechanical stop 744 may be coated or covered with a polymeric sealing material such as polyurethane, silicone, or other suitable polymer to aid in the formation of distal seal 748. Mechanical stop 744 may be adapted to have an engagement configuration that provides a friction-fit or snap-fit with the distal end of inflation catheter 740 or with a mating component disposed thereon.

Figure 8:
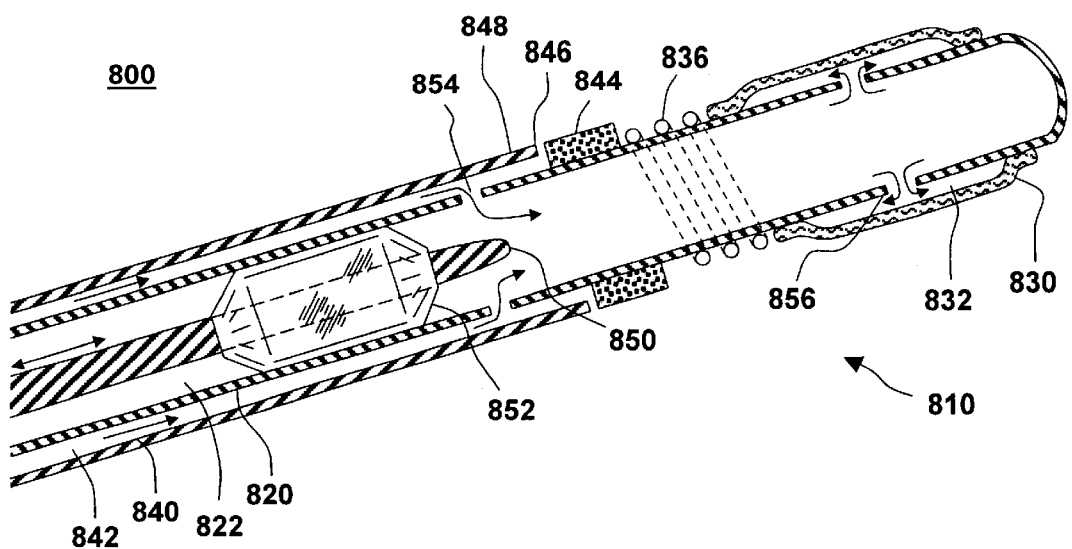
FIG. 8 shows a longitudinal cross-sectional view of a distal end of an occlusion catheter, in accordance with another embodiment of the current invention.

FIG. 8 shows a longitudinal cross-sectional view of a distal end of occlusion catheter 810, in accordance with another embodiment of the present invention at 800. Occlusion catheter 810 includes hollow guidewire 820 having central lumen 822, an inflatable occlusion balloon 830 attached proximate to a distal end of hollow guidewire 820, and an inflation catheter 840 slidable over hollow guidewire 820. Mechanical stop 844, comprising a band, collar or plate, is attached via sealing spring 836 to hollow guidewire 820 at a point near a proximal end of occlusion balloon 830. Distal seal 846 is made between a distal end of inflation catheter 840 and mechanical stop 844 when distal end 848 of inflation catheter 840 is pressed and abutted against mechanical stop 844, compressing sealing spring 836 and providing a leak-tight seal while occlusion balloon 830 is being inflated. Sealing spring 836 may comprise, for example, one or more turns of flexible stainless steel or nitinol. A gasket or other compliant material may be attached to the distal end of inflation catheter 840 or to a sealing surface of mechanical stop 844 to aid in the formation of distal seal 846.

In this embodiment, inflation fluid, which is injected into an annular inflation lumen 842 formed between hollow guidewire 820 and inflation catheter 840, flows through one or more inflation ports 854 positioned between annular inflation lumen 842 and central lumen 822 of hollow guidewire 820. Sealing plug 852 is attached to core wire 850, is centrally disposed within hollow guidewire 820, and can be positioned at a location proximal to inflation ports 854 to open the distal valve. Sealing plug 852 can also be positioned at a location distal to inflation ports 854 to close the valve, thereby blocking the flow of inflation fluid to and from interior region 832 of occlusion balloon 830 through one or more side ports 856 located between a distal portion of central lumen 822 and interior region 832 of occlusion balloon 830. Axial translation of sealing plug 852 to close the distal valve and block fluid flow between inflation port 854 and side ports 856 can be achieved by axially displacing a proximal end of core wire 850 with respect to hollow guidewire 820. Axial travel of sealing plug 852 can be limited, for example, by abutment of the distal end of core wire 850 against the sealed end of hollow guidewire 820 or with an external valve actuator.

Figure 9:
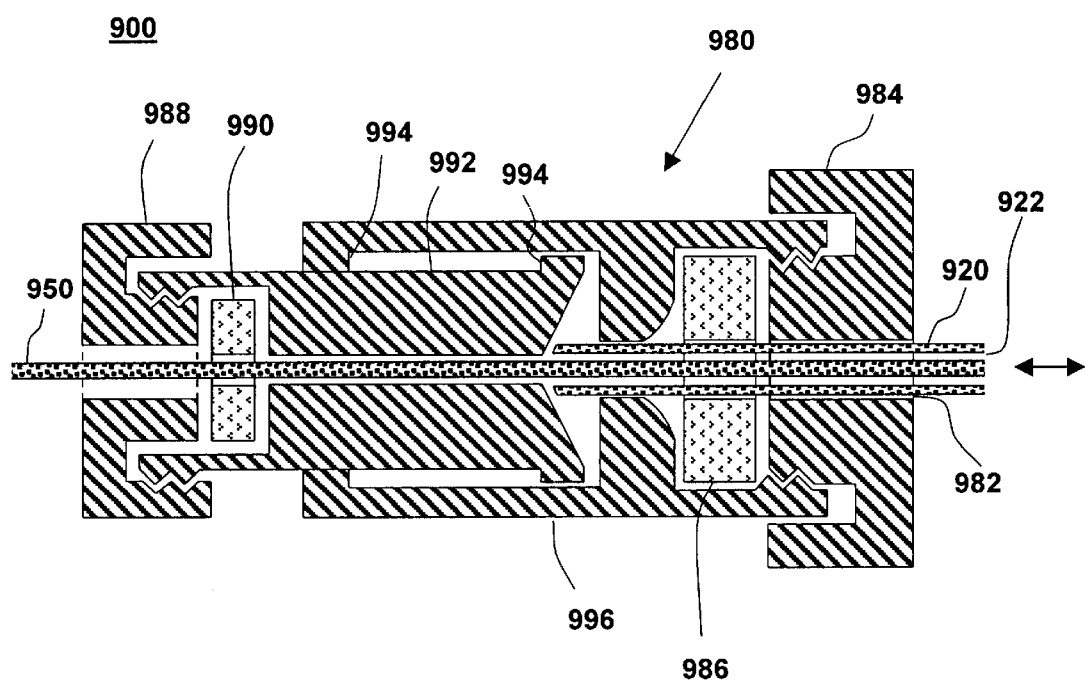
FIG. 9 illustrates a valve actuator at the proximal end of an occlusion catheter, in accordance with one embodiment of the current invention.

FIG. 9 illustrates one example of valve actuator 980 detachably coupled at the proximal end of an occlusion catheter, in accordance with the present invention at 900. Typically hand held, valve actuator 980 can be removably coupled to proximal ends of hollow guidewire 920 and core wire 950, the latter being disposed within central lumen 922 and extending from a proximal end of hollow guidewire 920. Valve actuator 980 actuates a distal valve (not shown) coupled to hollow guidewire 920 to control the flow of inflation fluid between hollow guidewire 920 and an inflatable occlusion balloon (not shown) attached proximate to a distal end of hollow guidewire 920. Axial displacement of the proximal end of core wire 950 with respect to the proximal end of hollow guidewire 920 results in the opening and closing of the distal valve.

In one example, valve actuator 980 couples to hollow guidewire 920 and core wire 950 by inserting hollow guidewire 920 with an extending core wire 950 into valve actuator hole 982. A hollow guidewire clamping mechanism comprising, for example, knurled knob 984 and an elastomeric ring 986, clamps gently and securely onto an outer surface of hollow guidewire 920. Tightening of knurled knob 984 compresses elastomeric ring 986 onto hollow guidewire 920. A core wire clamping mechanism comprising, for example, knurled knob 988 and an elastomeric ring 990, compresses and gently clamps elastomeric ring 990 securely onto an outer surface of core wire 950 when knurled knob 988 is tightened. Slidable piston 992 contained within an actuator body 996 can be pushed or pulled within actuator body 996 to axially displace core wire 950 within hollow guidewire 920, thereby actuating a distal valve. Actuator stops 994 positioned on slidable piston 992 and actuator body 996 limit the stroke and axial motion of core wire 950, avoiding excessive displacement of the distal valve and ensuring accurate operation of the distal valve. A proximal end of hollow guidewire 920 may be funneled through an inlet port of actuator body 996 and abutted against an angled surface of slidable piston 992 when the hollow guidewire 920 with extended core wire 950 are inserted into valve actuator 980.

Before or after insertion of the occlusion catheter into the body, valve actuator 980 may be attached to the proximal ends of hollow guidewire 920 and core wire 950 to actuate a distal valve that controls the flow of inflation fluid between hollow guidewire 920 and an occlusion balloon. For example, core wire 950 is threaded through valve actuator 980. Hollow guidewire 920 and an extended portion of core wire 950 are coupled to valve actuator 980. Core wire 950 may be retracted a predetermined distance from hollow guidewire 920 by axially displacing slidable piston 992 that opens the distal valve. When the distal valve is opened, inflation fluid may be sent through an annular inflation lumen formed between hollow guidewire 920 and an inflation catheter slid over hollow guidewire to inflate an occlusion balloon located at the distal end of hollow guidewire 920. When the balloon is inflated to the desired diameter, the distal valve is closed by inserting core wire 950 a predetermined distance into hollow guidewire 920.

FIG. 10 is a flow diagram of a method for treating a vascular condition, in accordance with one embodiment of the present invention at 1000. Vascular treatment method 1000 includes various steps to block or occlude a vessel within the body, and to allow subsequent treatment of one or more regions within the blocked vessel. Treatment of vascular conditions may include the prevention or correction of various ailments and deficiencies associated with the cardiovascular system, the cerebrovascular system, urogenital systems, biliary conduits, abdominal passageways and other biological vessels within the body.

An occlusion catheter is provided, as seen at block 1005. The occlusion catheter includes a hollow guidewire having a central lumen, an inflatable occlusion balloon attached proximate to a distal end of the hollow guidewire, and an inflation catheter slidable over the hollow guidewire. The occlusion catheter includes a distal valve. In one example, the distal valve includes a core wire with a sealing plug at a distal end of the core wire, the core wire slidably disposed within the hollow guidewire. An axial displacement of a proximal end of the core wire displaces the sealing plug at the distal end of the core wire to open and close the distal valve.

The occlusion balloon is positioned in a vessel of the body, as seen at block 1010. The hollow guidewire and inflation catheter are manually manipulated through the vascular system to the desired location for placement of the occlusion balloon. For example, an incision is made in the body near the femoral artery, and the hollow guidewire with the occlusion balloon and the inflation catheter is inserted through the incision, through the femoral artery, and into a position within a blood vessel where the balloon is to be inflated. The annular inflation lumen and other lumens may be purged with inflation fluid or contrast fluid prior to insertion of the occlusion catheter in the body.

When positioned in the vessel, inflation fluid such as saline solution or dilute contrast media is injected to inflate the occlusion balloon, as seen at block 1015. The inflation fluid is injected in part through an annular inflation lumen formed between the inflation catheter and the hollow guidewire.

When the distal valve is open, the inflation fluid flows through an inflation port into a distal portion of the central lumen, as seen at block 1020. Inflation fluid may flow through the annular inflation lumen and then through one or more inflation ports into the central lumen.

The inflation fluid flows through a side port in the hollow guidewire, as seen at block 1025. The side port is typically positioned between the central lumen and the occlusion balloon. One or more side ports allow inflation fluid to flow through the side ports into an interior region of the occlusion balloon.

The occlusion balloon is inflated with the inflation fluid, as seen at block 1030. As inflation fluid flows into the interior region of the occlusion balloon, the occlusion balloon enlarges in diameter, temporarily blocking the flow of bodily fluid through the vessel. The inflation fluid is typically pressurized through a port in the inflation catheter, inflating the occlusion balloon until the desired diameter is obtained. The occlusion balloon presses outwardly against the vessel wall and is secured in part by the tissue bed and vascular wall surrounding the inflated occlusion balloon. The position of an inflated or partially inflated balloon may be monitored, for example, with injections of radiopaque contrast fluid and associated x-ray imaging systems.

The distal valve is then closed, as seen at block 1035. When the occlusion balloon has been inflated, the distal valve is closed to retain inflation fluid within the occlusion balloon. The distal valve may be closed, for example by axial displacement of the sealing plug at the distal end of the hollow guidewire, positioning the sealing plug between the inflation port and the side port, and thereby blocking the central lumen of the hollow guidewire and preventing flow into or out of the occlusion balloon. The balloon is occluding and essentially anchored within the vessel, and the inflation catheter may be removed from the hollow guidewire.

To assist in providing an image of the vessel and any stenoses within the vessel, contrast fluid may be injected from the distal end of the inflation catheter, as seen at block 1040. In one embodiment of the occlusion catheter, a distal end of the inflation catheter and a mechanical stop coupled to the hollow guidewire proximal to the occlusion balloon cooperate to form a distal seal. When the inflation catheter is partially extracted from the hollow guidewire, the distal seal is broken and contrast fluid, often also used as inflation fluid, may be injected through the annular inflation lumen and out of the distal end of the inflation catheter. In another embodiment, a contrast fluid lumen coupled to the inflation catheter or integrally formed therein may be used to transport contrast fluid to a distal end of the inflation catheter. External x-ray monitoring equipment is used to produce an image of the vessel with the aid of the stagnant column of radiopaque fluid proximal to the inflated occlusion balloon. Alternatively, the distal end of the inflation catheter may be used to aspirate and remove thrombotic material and emboli from within the vessel through the annular inflation lumen while the occlusion balloon remains enlarged and occludes the vessel.

To remove the inflation catheter while retaining the hollow guidewire in an anchored position, a valve actuator is detached from a proximal end of the hollow guidewire, as seen at block 1045. The valve actuator comprises a mechanism that actuates the distal valve. Detaching the valve actuator allows the inflation catheter to be extracted from the body and slid off the hollow guidewire.

The inflation catheter may then be removed, as seen at block 1050. The inflation catheter may be, for example, an over-the-wire (OTW) type of catheter, a rapid-exchange catheter, or a zipper-style catheter that allow removal of the inflation catheter from the hollow guidewire.

Additional contrast fluid may be injected from the distal end of the hollow guidewire for stenosis visualization, as seen at block 1055. In one example, one or more contrast fluid injection ports in the side of the hollow catheter proximal to the sealing plug of the distal valve may be used to inject additional contrast fluid into the stagnant fluid within the vessel after the inflation catheter is slidably removed from the hollow guidewire. Since the inflated balloon blocks the vessel, a smaller amount of contrast fluid may be required in comparison with other methods available for visualizing the vessel and associated stenoses. The contrast fluid may be sent through the central lumen of the hollow guidewire, albeit partially restricted by the core wire that is centrally disposed within the hollow guidewire. The inflation port may also be used for injecting the additional contrast fluid.

Additional treatment steps may be added to the method for treating a vascular condition. For example, treatment catheters such as stent-delivery catheters can be inserted over the hollow guidewire and brought into position within the body at the desired location in the vessel. When the final treatment step is completed, the occlusion catheter and the hollow guidewire are removed from the body. For example, the occlusion catheter can be removed by reattaching the valve actuator, opening the distal valve, deflating the occlusion balloon by allowing the elastic restoring forces of the occlusion balloon to expel the inflation fluid, and withdrawing the hollow guidewire with the collapsed occlusion balloon from the body. Optionally, the balloon can be deflated by reloading the inflation catheter over the hollow guidewire such that aspiration or partial vacuum can be used to withdraw inflation fluid through the opened distal valve and from the balloon.

Variations and alterations in the design, manufacture and use of the occlusion catheter and the distal valve are apparent to one skilled in the art, and may be made without departing from the spirit and scope of the present invention. While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for treating a vessel in a body, comprising:
   a hollow guidewire having a central lumen;
   an occlusion balloon attached proximate to a distal end of the hollow guidewire; and
   an inflation catheter slidable over the hollow guidewire, wherein an annular inflation lumen formed between the inflation catheter and the hollow guidewire fluidly communicates with the central lumen of the hollow guidewire, allowing inflation fluid to flow through the annular inflation lumen and into a distal portion of the central lumen to inflate the occlusion balloon.

2. The system of claim 1 wherein the inflation catheter is removable from the hollow guidewire.

3. The system of claim 1 wherein the annular inflation lumen fluidly communicates with the central lumen of the hollow guidewire through an inflation port positioned between the annular inflation lumen and the central lumen of the hollow guidewire.

4. The system of claim 1 wherein the central lumen of the hollow guidewire fluidly communicates with an interior region of the occlusion balloon through a side port in the hollow guidewire, the side port positioned between the central lumen of the hollow guidewire and the occlusion balloon.

5. The system of claim 1 further comprising:
   a distal valve coupled to the hollow guidewire to control the flow of inflation fluid between the hollow guidewire and the occlusion balloon.

6. The system of claim 5 wherein the distal valve comprises a core wire with a sealing plug at a distal end of the core wire, the core wire slidably disposed within the hollow guidewire, and wherein an axial displacement of a proximal end of the core wire displaces the sealing plug at the distal end of the core wire to open and close the distal valve.

7. The system of claim 5 further comprising:
   a valve actuator detachably coupled at a proximal end of the hollow guidewire to actuate the distal valve.

8. The system of claim 1 further comprising:
   a mechanical stop coupled to an exterior surface of the hollow guidewire proximal to the occlusion balloon, wherein the mechanical stop limits an axial displacement of the inflation catheter over the hollow guidewire.

9. The system of claim 8 wherein the mechanical stop and a distal end of the inflation catheter cooperate to form a distal seal between the inflation catheter and the hollow guidewire.

10. The system of claim 1 further comprising:
    a contrast fluid lumen extending through the inflation catheter to transport contrast fluid to a distal end of the inflation catheter.

11. The system of claim 1 further comprising:
    a contrast fluid injection port positioned near the distal end of the hollow guidewire, wherein contrast fluid from the central lumen of the hollow guidewire is injected through the contrast fluid injection port when the inflation catheter is slidably removed from the hollow guidewire.

12. An occlusion catheter for blocking flow through a vessel, comprising:
    a hollow guidewire having a central lumen;
    an occlusion balloon attached proximate to a distal end of the hollow guidewire; and
    an inflation catheter slidable over the hollow guidewire, wherein an annular inflation lumen formed between the inflation catheter and the hollow guidewire fluidly communicates with the central lumen of the hollow guidewire, allowing inflation fluid to flow through the annular inflation lumen and into a distal portion of the central lumen to inflate the balloon.

13. The occlusion catheter of claim 12 further comprising:
    a distal valve, wherein the distal valve includes a core wire with a sealing plug at a distal end of the core wire, the core wire slidably disposed within the hollow guidewire, and wherein an axial displacement of a proximal end of the core wire displaces the sealing plug at the distal end of the core wire to open and close the distal valve.

14. The occlusion catheter of claim 13 further comprising:
    a valve actuator detachably coupled at a proximal end of the hollow guidewire to actuate the distal valve.

15. A method for treating a vascular condition, comprising:
    providing an occlusion catheter, the occlusion catheter including a hollow guidewire having a central lumen, an occlusion balloon attached proximate to a distal end of the hollow guidewire, and an inflation catheter slidable over the hollow guidewire;
    injecting an inflation fluid through an annular inflation lumen formed between the inflation catheter and the hollow guidewire;
    flowing the inflation fluid through an inflation port into a distal portion of the central lumen;
    flowing the inflation fluid through a side port in the hollow guidewire, the side port positioned between the central lumen of the hollow guidewire and the occlusion balloon; and
    inflating the occlusion balloon with the inflation fluid.

16. The method of claim 15 further comprising:
    closing a distal valve when the occlusion balloon is inflated to retain inflation fluid within the occlusion balloon.

17. The method of claim 15 further comprising:
    injecting contrast fluid from a distal end of the inflation catheter.

18. The method of claim 15 further comprising:
    detaching a valve actuator from a proximal end of the hollow guidewire.

19. The method of claim 15 further comprising:
    removing the inflation catheter from the hollow guidewire after the balloon is inflated.

20. The method of claim 15 further comprising:
    injecting contrast fluid from a contrast fluid injection port after the inflation catheter is removed from the hollow guidewire, wherein the contrast fluid injection port is proximal to the occlusion balloon.

* * * * *